US00PP15580P2

(12) United States Plant Patent
Nakata

(10) Patent No.: US PP15,580 P2
(45) Date of Patent: Feb. 22, 2005

(54) PLUM TREE NAMED 'AUGUST GIANT'

(50) Latin Name: *Prunus salicina*
Varietal Denomination: August Giant

(76) Inventor: Harry Nakata, 2221 Carolyn St., Kingsburg, CA (US) 93631

( * ) Notice: Subject to any disclaimer, the term of this patent is extended or adjusted under 35 U.S.C. 154(b) by 82 days.

(21) Appl. No.: 10/751,213

(22) Filed: Dec. 30, 2003

(51) Int. Cl.[7] ..... A01H 5/00
(52) U.S. Cl. ..... Plt./184
(58) Field of Search ..... Plt./184

(56) References Cited

U.S. PATENT DOCUMENTS

PP5,744 P 5/1986 Zaiger et al.

*Primary Examiner*—Anne Marie Grunberg
(74) *Attorney, Agent, or Firm*—Mark D. Miller

(57) ABSTRACT

A new and distinct variety of plum tree that is characterized by producing a freestone fruit with good dark red coloration and that is ripe for commercial harvesting and shipment August 28–30 in the San Joaquin Valley of Central California. The new variety is closely similar to the 'Mid Red' plum tree (U.S. Plant Pat. No. 2,744) from which it is a bud sport and from which is distinguishable in that the fruit is much larger, has more dark coloration, has excellent flavor and stores exceptionally well, ripening seven days after 'Mid Red' plum fruit.

1 Drawing Sheet

BACKGROUND OF THE NEW VARIETY

The present invention refers to a new variety of plum which will hereinafter be denominated as the 'August Giant' plum tree. The 'August Giant' is a yellow-red fleshed plum freestone fruit that is mature for harvesting and shipping during the August 28–30 period in a normal year in the San Joaquin Valley of Central California as a large fruit with red blush and yellow flesh.

In the development of new commercial varieties, specific characteristics provide a premium on these fruit varieties that mature early or late in the growing season. However, in particular early varieties lack size, flavor and coloration on blush. Therefore in order for a fruit to be a commercial success, it must be of good size, good color, and also have good holding/storage and shipping characteristics. In additional, the date of maturing must be different from other similar fruit. This new invention meets all of the aforementioned criteria and therefore would be of commercial appeal to the consumer.

ORIGIN AND ASEXUAL REPRODUCTION OF THE NEW VARIETY

The present invention (variety) was discovered by the inventor on his four acre plum planting of 'Mid Red' variety (U.S. Plant Pat. No. 5,744) which is located near Parlier, Calif. in the San Joaquin Valley of Central California. The invention was discovered as a bud sport of 'Mid Red' in 1999. The new variety was asexually reproduced in the dormant season of 2000/2001 by bud grafting three trees on Nemaguard rootstock in a plum planting about one third of a mile from the original planting. Another eight trees were grafted in the dormant season of 2001/2002 approximately 1¾ miles south of the original source orchard. The inventor carefully compared the asexually reproduced trees with the parent sport including the fruit and found they are identical in all respects.

SUMMARY OF THE NEW VARIETY

The 'August Giant' plum tree is characterized by producing a large freestone fruit which has very good blush coloration and is ripe for commercial harvesting or shipping around August 28–30 in a normal year in the San Joaquin Valley of Central California as a large fruit with red blush and yellow flesh. The new variety is most similar to 'Mid Red' plum tree (U.S. Plant Pat. No. 5,744) from which it is a sport bud, but from which it is distinguishable in that it ripens approximately seven (7) days after the 'Mid Red' variety. The fruit of this new variety is large, with good flavor and good red color, which makes it greatly acceptable for the consumer.

BRIEF DESCRIPTION OF THE DRAWING

The accompanying, a colored photograph, shows in three different views the bottom or stem end of the fruit, the apex of the fruit, and the suture side of the fruit. In addition, at the bottom of the photograph is a fruit cut in half displaying the pit well on the left and the pit in the pit well on the right with a single pit in the middle and, finally, the foliage of the new variety of plum tree.

DETAILED DESCRIPTION

Referring more specifically to the horticultural details of the new and distinct variety of plum trees, the following descriptions have been observed under the ecological conditions prevailing at the origin orchard which is located near Parlier, Calif. in the San Joaquin Valley of Central California. All major color designations are by reference to the Dictionary of Color by Maerz and Paul, First Edition, published in 1930. Common colors are also employed.

Tree

Size: Medium, for 3rd leaf tree 8–10 feet high 6–8 feet wide.
Vigor: Good.
Shape: Pyramid—upright.

Productivity: Very good for 3rd leaf tree with regular bearing.
Chilling requirements: Normal for plum trees in the Central San Joaquin Valley of California.

Trunk

Size: Medium—14½ inches circumference, 12 inches above ground.
Surface texture: Rough.
Color code: Near Wineberry (55-E-4).
Lenticels: Many.

Branches

Size: Medium, 6–8 inches in circumference.
Angle of branches: 52°.
Color of branches over 1 year old: Pigeon (55-A-3).
Color of branches less than 1 year old: Rainette Green (21-K-4).

Leaves

Size: Medium-large.
*Length.*—105–115 mm (4.13–4.53 inch).
*Width.*—44–58 mm (1.732–2.28 inch).
Shape: Ovate.
*Margin.*—Double serration.
Glands: 2 reniform—small reddish brown.
Stipules: 2 large—10 mm (0.39 inch).
*Color.*—Turtle Green (19-C-5).
Color: Upper surface—Chrome Green deep (24-H-12). Lower surface—Spinach Green (22-H-7).
Petiole: Length: 11–15 mm (0.43–0.59 inch).
*Diameter.*—2 mm (0.08 inch).
*Color.*—Rainette Green (21-K-4).
Midvein: Width: 1½ mm (0.04–0.06 inch).
*Color.*—Rainette Green (21-K-4).

Flowers

Flower buds:
*Shape.*—Conic.
*Size.*—Length 5 mm (0.2 inch) average.
*Width.*—3–5 mm (0.12–0.2 inch).
Calyx: 5 sepals.
*Color.*—Sea Green (19-K-6).
Flowers: Generally showy type.
Date of first bloom: 10%—12% by February 28; 100% by March 8.
Flowers: Small—in clusters of three to five.
*Diameter when fully opened.*—22 mm average (0.87 inch).
*Bloom.*—Quantity—abundant.
Petals: 5
*Size.*—Small.
*Length.*—8–10 mm (0.31–0.39 inch).
*Width.*—7–9 mm (0.28–0.35 inch).
*Form.*—Broadly ovate.
*Color.*—White.
*Claws.*—Small—1 mm (0.04 inch) truncate.
*Petal margins.*—Undulate — rounded at tip.
*Pedicel.*—5 mm (0.2 inch) average. Color: Calliste Gr. (19L-6).
*Sepals.*—Color — Sea Green (19-K-6).
*Stamen.*—18–22.
*Filament.*—White.
*Anthers.*—Small. Color: Yellow Ochre (11-L-7).
*Pistil.*—Shorter in length than stamens. Color: Sky Green (18-I-5)
*Fertility.*—Self fertile — no pollinator required.

Fruit

Date of maturity: August 28–30.
Size: Large.
*Diameter of axial plane.*—62–68 mm (2.44–2.68 inches).
*Transverse in suture plane.*—65–70 mm (2.56–2.76 inches).
*Transverse at right angle to suture plane.*—68–72 mm (2.68–2.83 inches).
Form: Nearly uniform. Nearly symmetrical. Ventral surface—smooth.
Stem cavity:
*Length.*—16–18 mm (0.63–0.71 inch).
*Width.*—12–16 mm (0.47–0.63 inch).
*Depth.*—8–10 mm (0.31–0.39 inch).
Stem:
*Length.*—8–11 mm (0.31–0.43 inch).
*Width.*—2 mm (0.08 inch).
*Apex.*—Slightly pointed.
*Pistil pt..*—Noticeable.
*Skin.*—Thickness normal for plum.
*Texture.*—Firm.
Color:
*Blush color.*—De'Medici (54-L-12). Rubient (55-L-8). Ground color—Lime Y (11-L-5).
*Flesh color.*—Near skin — Chianti Antique Rube (6-L-6). Remainder — Antique Gold (12-L-8).
*Color at surface of cavity.*—Antique Gold/Golden Y (12-L-8).
*Color of pit well.*—Peruvian Gold (13-L-11).
Pit well:
*Length.*—23 mm (0.91 inch).
*Width.*—17 mm (0.67 inch).
*Depth.*—6–7 mm (0.24–0.28 inch).

Stone

Freestone: Fibers—few.
Size:
*Length.*—23 mm (0.91 inch).
*Width.*—16–18 mm (0.63–0.71 inch).
*Thickness.*—10 mm (0.39 inch).
Form—ovate.
Apex shape—somewhat rounded and somewhat pointed.
Color—(dry) Mellow Gold (10-L-6).
Base—flattened.
Sides—Ventral side winged. Dorsal side ridged from apex to base.
Surface—slightly grooved at basal end.
Tendency to split—None observed.
Use—Fresh market.
Keeping quality—Excellent.
Resistance to disease—Unknown.
Harvest date: August 28–30. Has not been sold. Variety has not been publicly used or exhibited. No reproductive parts have been given away.
Name of new variety: 'August Giant'.

The above description of this new variety of plum tree is based on the growing conditions prevalent in the Parlier area of the San Joaquin Valley of Central California; variations of the usual magnitude, such as differences in maturity date and production, may be due to cultural practices including irrigation, fertilization, pruning, fruit thinning and primary climate changes.

What is claimed is:

1. A new and distinct variety of plum tree as described and illustrated that is somewhat similar to the 'Mid Red' plum tree from which it is a bud sport, but is distinguished therefrom in that the fruit is larger, has more dark red coloration, has excellent flavor and stores exceptionally well, ripening about seven days after 'Mid Red' plum fruit.

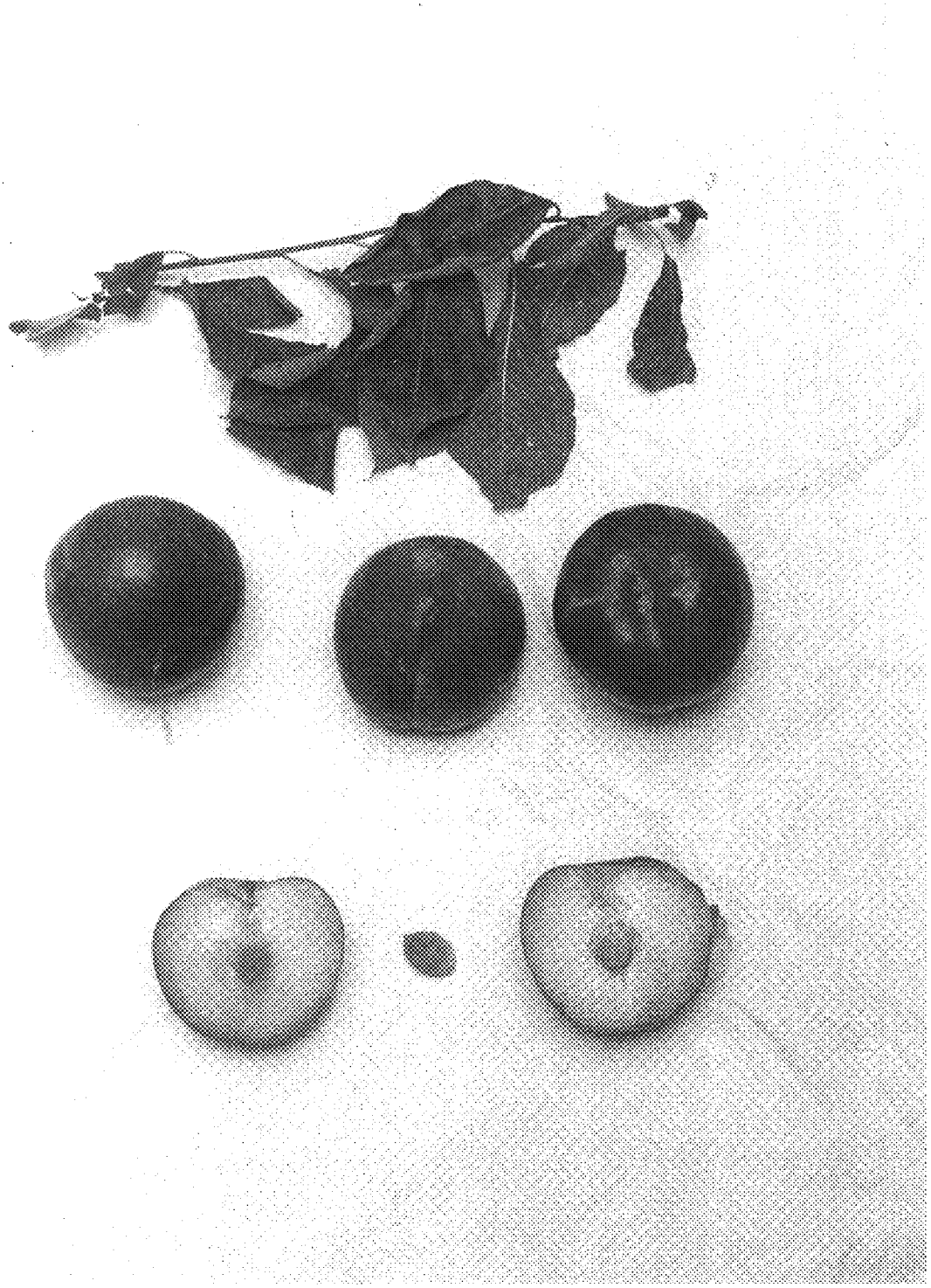

* * * * *